United States Patent [19]
Takahashi et al.

[11] Patent Number: 5,523,213
[45] Date of Patent: Jun. 4, 1996

[54] METHOD FOR COMPUTING MORPHOLOGY OF CORNEA ENDOTHELIUM CELLS

[75] Inventors: Yoko Takahashi; Tatsuya Kasahara, both of Hyogo, Japan

[73] Assignee: Konan Inc., Hyogo, Japan

[21] Appl. No.: 216,553

[22] Filed: Mar. 23, 1994

[30]  Foreign Application Priority Data

Mar. 23, 1993 [JP] Japan .................................. 5-089244

[51] Int. Cl.[6] .............................. C12Q 1/02; C12Q 1/08; G01B 11/26
[52] U.S. Cl. .......................... 435/40.5; 435/29; 435/39; 356/138; D24/172
[58] Field of Search .............................. 435/29, 39, 40.5; D24/172; 356/138

[56]  References Cited

PUBLICATIONS

Matsuda et al. Arch Opthalmol. vol. 103 (1985) (pp. 68–70).
"Wentworth Plane and Solid Geometry" Ginn & Company, Boston, (1911) p. 218 and p. 223.

*Primary Examiner*—Donald E. Czaja
*Assistant Examiner*—Jane Williams Elkin

[57]  ABSTRACT

In examining the progress of patients before and after a cataract operation, the morphology of cornea endothelium cells used in medical treatment, may be determined from a cornea endothelium cell image with less labor. Center points of two-dimensionally continuous cells of a cornea endothelium cell image are entered into a computer, and peripheral points obtained by determining peripheral points which are center points of the cells within a specified distance from one center point are sorted clockwise. If an angle formed by successive two peripheral points and the center point is less than a specified angle, the greater of the two peripheral points in distance from the center point is excluded from the peripheral points. If a distance between the first point and the third point of the obtained successive three peripheral points is shorter than a distance between the center point and the second point, the second point is excluded from the peripheral points, and average distances between the peripheral points and the center point are determined. A perpendicular line that proportionally divides a distance between a center point and its peripheral points by their average distances to the peripheral points is determined for each of the successive peripheral points, and intersection points of the resulting perpendicular lines are determined as vertices of the cells. Thus, morphological data are computed from the obtained vertices.

16 Claims, 6 Drawing Sheets

METHOD FOR COMPUTING MORPHOLOGY OF CORNEA ENDOTHELIUM CELLS

FIELD OF THE INVENTION

The present invention relates to a method for quantitatively computing morphology of cornea endothelium cells to provide decision data to doctors, in examining the progress of patients before and after a cataract operation in the ophthalmic field of medical treatment.

BACKGROUND OF THE INVENTION

As the number of older people increases, the number of cataract patients has increased. It is common practice that cornea endothelium cells are checked before and after a cornea operation. The conventional check uses specular photography (photography of cornea endothelium cells by reflected rays of light that has been projected on the cornea), in which the following methods are used to obtain decision reference data:

1. Grid method—with a grid superimposed on a magnified photograph of cornea endothelium, the number of cells in the grid of specified intervals is counted and converted into the number of cells per mm$^2$ (cell density);

2. Cell sizer method—a model whose cell density and coefficient of variation (CV) are known is previously prepared, and the cell density and the CV are determined by comparing it with the cornea endothelium photograph;

3. Digitizer method—coordinates of vertices of a cell (e.g. coordinates of points 1, 2, 3, 4, 5, and 6, which are vertices of the profile of a hexagonal cell as shown in FIG. 1) are entered into a computer, and the correct morphology of the individual cells is determined by the following equations:

Equation 1

$$\text{Cell area: } Ar = \frac{1}{2} \Sigma((X_n \times Y_{n+1}) - (X_{n+2} \times Y_n)) \ (\mu m^2)$$

Equation 2:
Average cell area:

$$Ave = \frac{\Sigma Ar}{N} \ (\mu m^2), \ N: \text{ the number of cells}$$

Equation 3

$$\text{Cell density: } CD = 1000000/Ave \ (pcs/M^2)$$

Equation 4:

$$\text{Standard deviation: } SD = \frac{\Sigma (Ave - Ar_n)^2}{N-1}$$

Equation 5

$$\text{Coefficient of variation: } CV = SD/Ave$$

Equation 6
Hexagonal cell frequency:

$$Ap_6 = (\text{number of hexagonal cells})/N; \text{ and}$$

4. Opposite-side input method—using the midpoints $a_c$, $b_c$, $C_c$, and $d_c$ of opposite two sides of mutually adjoining cells A, B, D, and D (as illustrated in FIG. 2), the cell area is approximated by determining the area of an equilateral hexagon circumscribing a circle whose diameter is formed by each pair of midpoints. In this case, for example, the area of the cell A is as follows:

Equation 7:

$$\text{Area of cell } A: Ar = \frac{\sqrt{3}}{2} \overline{ab^2} \ (\mu m^2)$$

The above-described conventional methods have the following problems:

1. The grid method allows only the determination of cell density;

2. The cell sizer method, although allowing determination of cell density and coefficient of variation, results in variations among persons who perform the comparison and therefore, may generate incorrect values;

3. The digitizer method, although obtaining all morphological data needed for clinical treatment necessitates a great deal of input labor, which is unsuitable for practical use; and 4. The opposite-side input method, although requiring less input, does not generate the polygonal number (hexagonal cell frequency, which is a decision criterion for doctors).

The present invention has been developed in view of the above-mentioned problems. An object of the present invention is therefore to provide a method for computing morphology of cornea endothelium cells, which solves the various disadvantages of the conventionally practiced methods and which allows profiles of cells to be reproduced simply by entering center points of the cells of a two-dimensional continuous cell image, so that all morphological data needed for clinical treatment equivalent to the digitizer method can be obtained with input labor far less than in the digitizer method.

To achieve the above object, the present invention provides a method for computing morphology of cornea endothelium cells, comprising the steps of:

(a) determining peripheral points within a specified distance from a center point of a selected one of the plurality of cells;

(b) sorting the peripheral points in a predetermined direction;

(c) determining an angle formed by first and second successive peripheral points in the predetermined direction and the center point;

(d) determining a first distance between the first successive peripheral point and a third successive peripheral point in the predetermined direction and a second distance between the center point and the second successive peripheral point;

(e) excluding one of the first and second successive peripheral points which is further from the center point, if the angle is less than a specified angle;

(f) excluding the second successive peripheral point if the first distance is less than the second distance;

(g) repeating steps (a)–(f) for remaining cells surrounding the selected one of the plurality of cells;

(h) determining an average distance between remaining peripheral points and the center point;

(i) determining a first point on a first line, connecting the center point and a first remaining peripheral point, by proportionally dividing a distance between the center point and the first remaining peripheral point according to the average distance between the remaining peripheral points and the center point and determining a first perpendicular line, perpendicular to the first line at the first point;

(j) determining a second point on a second line, connecting the center point and a second remaining peripheral point by proportionally dividing a distance between the center point and the second remaining peripheral point according to the average distance between the remaining peripheral points and the center point and determining a second perpendicular line, perpendicular to the second line at the second point;

(k) determining a first vertex of the selected one of the plurality of cells at an intersection of the first perpendicular line and the second perpendicular line;

(l) repeating steps (i)–(k) for each remaining peripheral point to determine all vertices of the selected one of the plurality of cells; and (m) determining the morphology of the plurality of cells from coordinates of all vertices of the selected one of the plurality of cells.

To further achieve the above object, the specified distance is of 2.5 to 3.5 times a distance from the center point to a closest peripheral point.

To further achieve the above object, the specified angle is 20 to 40 degrees.

To further achieve the above object, if the angle formed by the first and second peripheral points in the predetermined direction and the center point is greater than 90 to 110 degrees, the center point is a center point of a peripheral cell.

To further achieve the above object, when an angle formed by the first successive peripheral point, the center point, and the third successive peripheral point is greater than 120 to 140 degrees, the second peripheral point is retained.

To further achieve the above object, the first and second points are determined by proportionally dividing according to a square to a fourth power of the average distances.

To further achieve the above object, the plurality of cells are cornea endothelium cells.

To further achieve the above object, the predetermined direction is clockwise or counter-clockwise.

SUMMARY OF THE INVENTION

In the method for computing morphology of cornea endothelium cells according to the present invention, for each center point of a two-dimensional continuous cell image such as a cornea endothelium cell photograph, the center points are entered into a computer, peripheral points, which are cell centers within a specified distance from one center point are determined to include actual peripheral cells, and the resulting set of peripheral points (including peripheral points on the outer peripheral of actual peripheral points) is sorted clockwise or counterclockwise.

When the angle formed by two successive peripheral points and the center point is less than a specified angle, either of the two peripheral points is excluded from the set of peripheral points depending on which is further from the center point. When a distance between a first peripheral point and a third peripheral point obtained in the preceding step is shorter than a distance between a second peripheral point and a center point, the second point is excluded from the set of peripheral points, and the remaining peripheral points make up the actual peripheral points from which a cell-like configuration is correctly determined, where the cell which is originally an equilateral hexagon is transferred into triangular to ten-odd polygons. Then, average distances between the actual peripheral points obtained and the center point are determined. Further, a perpendicular line which proportionally divides a distance between the center point and a peripheral point by their average distances to the peripheral points is determined for the successive peripheral points. By further determining intersection points of the resulting perpendicular lines, vertices of the cell profile can be obtained. From the coordinates of the vertices, quantitative morphological data on the cornea endothelium cells can be computed.

In the step for determining peripheral points within a specified distance from a center point, the specified distance is set to a distance between 2.5 to 3.5 times the distance from the center point to the shortest peripheral point. This is the shortest distance that allows actual peripheral cells to be necessarily included, and to be efficiently tested. When the angle formed by successive two peripheral points and the center point is less than a specified angle, excluding either of the two peripheral points, whichever longer in distance from the center point, the specified angle is set to a value of 20 to 40 degrees.

Further, when the angle formed by successive two peripheral points and the center point is less than a specified angle, excluding from the peripheral points either of the two peripheral points, whichever longer in distance from the center point, when the angle formed by the successive two peripheral points and the center point is greater than a value of 90 to 110 degrees, the center point is taken as peripheral cell, so that the cell is suppressed from being reproduced.

Still further, when a distance between the first point and the third point of successive three peripheral points is shorter than a distance between the center point and the second point, excluding the second point from the peripheral points, when the angle formed by the first point, the center point, and the third point is greater than a value of 120 to 140 degrees, suppressing the second point from being excluded from the peripheral points.

These steps are well matched to actual cases, experimentally, making it possible to effectively determine actual peripheral points. Furthermore, in the step for determining a perpendicular line which proportionally divides a distance between the center point and a peripheral point by their average distances to the peripheral points, respectively for the successive peripheral points, to thereby determine intersection points of the resulting perpendicular lines as vertices of profiles of the cells, the step further includes weighting proportional allotment with values of the square to fourth power of the average distances and performing proportional division with the resulting value. This step is also well matched to actual cases.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

Embodiments of the present invention are now described with reference to the accompanying drawings.

Figure 1:
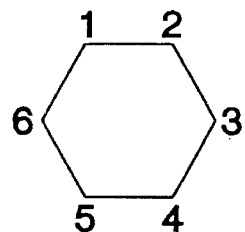
FIG. 1 illustrates entering vertices of the profile of a cell by the digitizer method.
Figure 2:
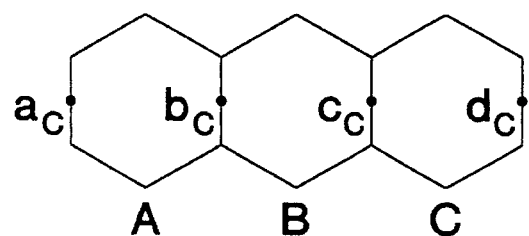
FIG. 2 illustrates entering midpoints of two opposite sides of a cell by the opposite-side input method.
Figure 3:
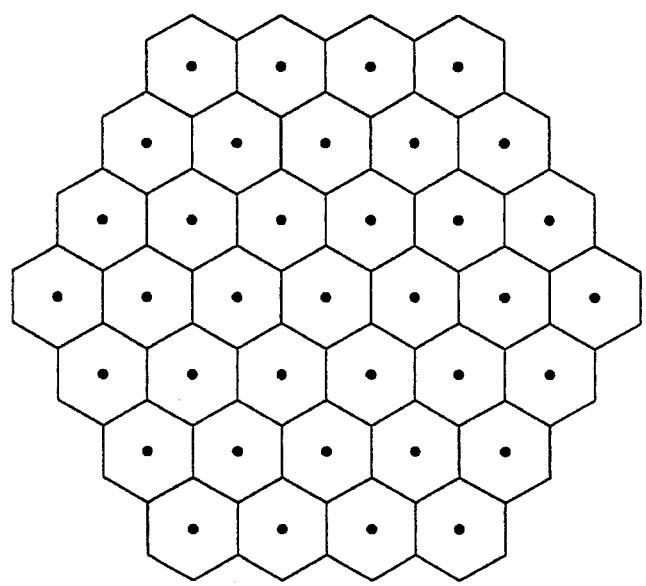
FIG. 3 illustrates entering center points of cells of a two-dimensionally continuous cornea endothelium cell image.

FIG. 3 shows a schematic diagram of a cell image when center points of cells of a two-dimensional continuous cornea endothelium cell image such as a cornea endothelium cell photograph are entered into a computer. The cell is originally an equilateral hexagon and deformed into triangular to ten-odd polygons (See FIG. 9). In FIG. 3, however, the cell image is assumed to be a group of equilateral hexagonal cells and input points of the cells are represented by black points.

Figure 4:
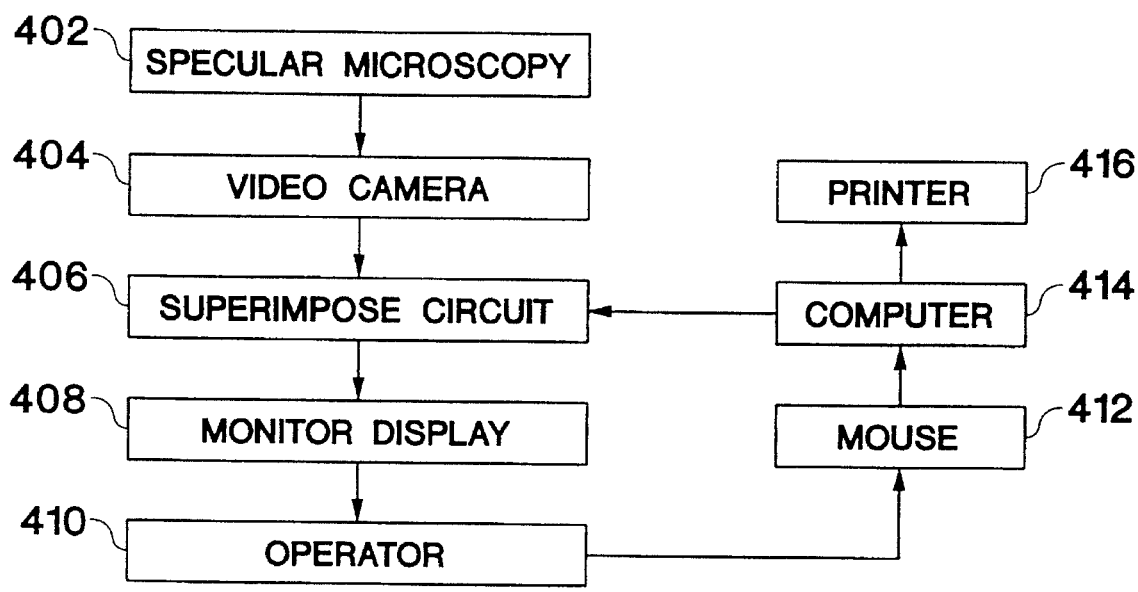
FIG. 4 also illustrates entering center points of the cells.

FIG. 4 illustrates entry of the center points of the cells. In this case, specular microscopy 402 which is a cornea endothelium cell photography, is photographed by a video camera 404. A video signal of a cornea endothelium cell image from the video camera 404 is fed to a superimpose circuit 406, and the cell image is displayed on a monitor 408. Further, when an operator 410 moves a mouse 412, a resulting movement signal is fed to a computer 414, and a movement signal of a cross mark due to the movement of the mouse 412 is fed to the superimposed circuit 406 from the computer 414 so as to be superimposed on the image signal of cornea endothelium cells derived from the video camera 404. Accordingly, the operator 410 can move the cross mark onto the cornea endothelium cell image on the monitor display 408, by moving the mouse 412. With the center of the cross mark positioned at a center (a black point in FIG. 3 as described above) of the cell image, the operator 410 enters coordinates of the center of a cell by pressing a button of the mouse 412. This input operation is effected for every cell center (200 times for 200 cells). With cell centers entered in this way, the computer 414 determines vertices of the profile of each cell, and performs the computations as shown in equations 1 through 6 from the obtained coordinates of vertices to compute quantitative morphological data on the cells. The computer 414 then prints out the obtained data to printer 416.

Figure 5:
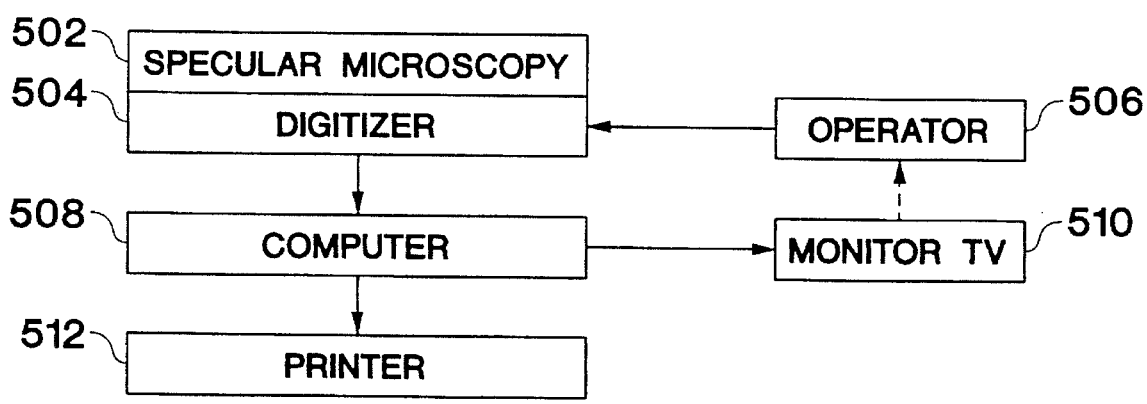
FIG. 5 is another system diagram for entering center points of the cells.

FIG. 5 illustrates another embodiment for entry of center points of the cells. In this case, specular microscopy 502, which is cornea endothelium cell photography, is placed on the upper plate surface of a digitizer 504. The operator 506 moves the cursor of the digitizer 504, so that the center of a cross mark cited at a transparent portion of the cursor is positioned at the center point of each cell image. In this state, the operator 506 presses the button for the cursor to enter coordinates of the center point into a computer 508. In doing this, instructions to the operator 506 are displayed on a monitor 510 connected to the computer 508, allowing the operator 506 to manipulate the computer 508 according to computer instructions. With center points of the cells entered in this way, the computer 508 operates as in the foregoing embodiment to compute the aforementioned quantitative morphological data of the cells and prints out the data on printer 512.

Figure 6:
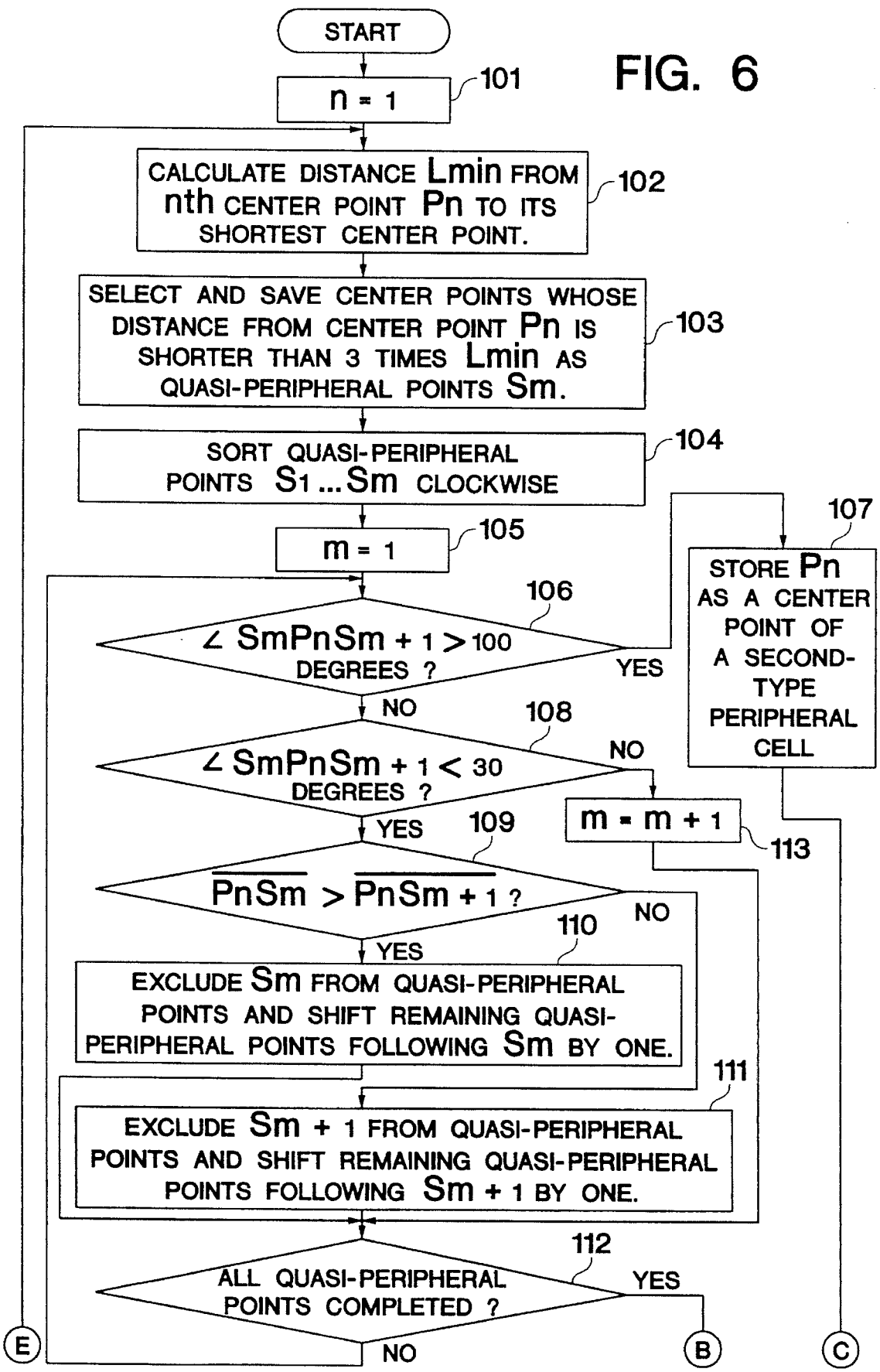
FIG. 6 is a flow chart showing the steps performed in one embodiment of the present invention.
Figure 7:
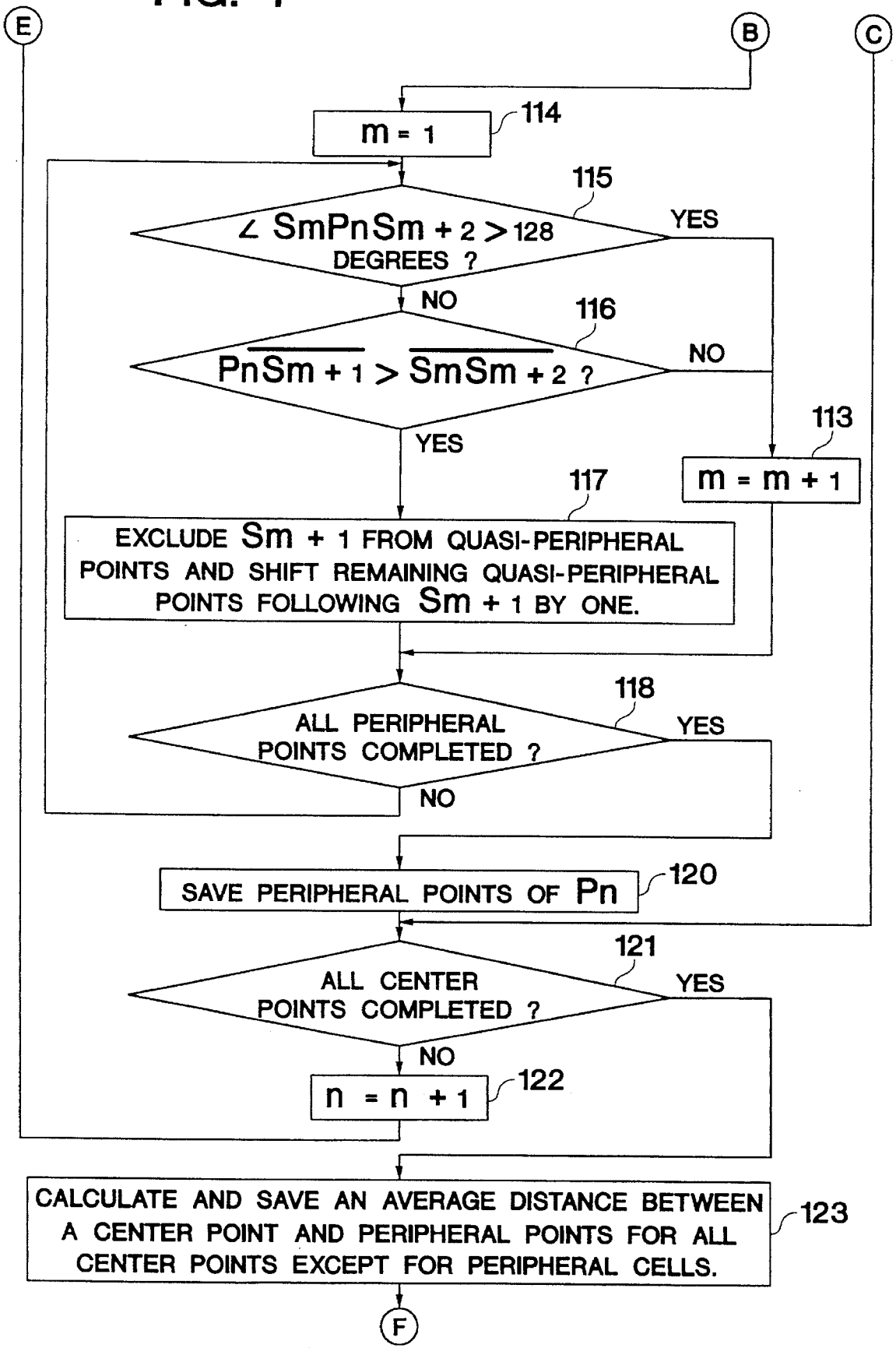
FIG. 7 is a flow chart of additional steps performed subsequent to the steps in FIG. 6.
Figure 8:
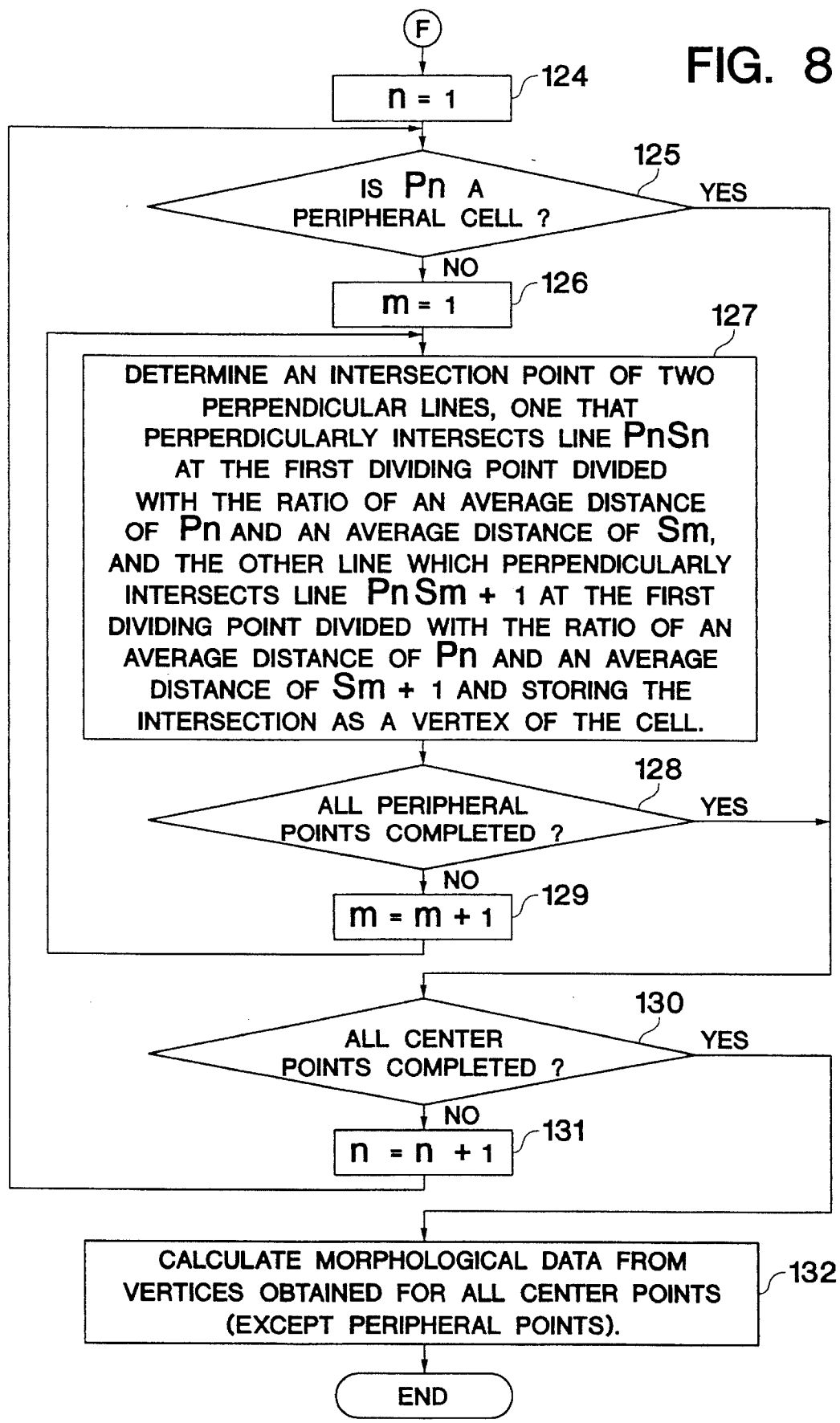
FIG. 8 is a flow chart of additional steps performed subsequent to the steps in FIG. 7.
Figure 9:
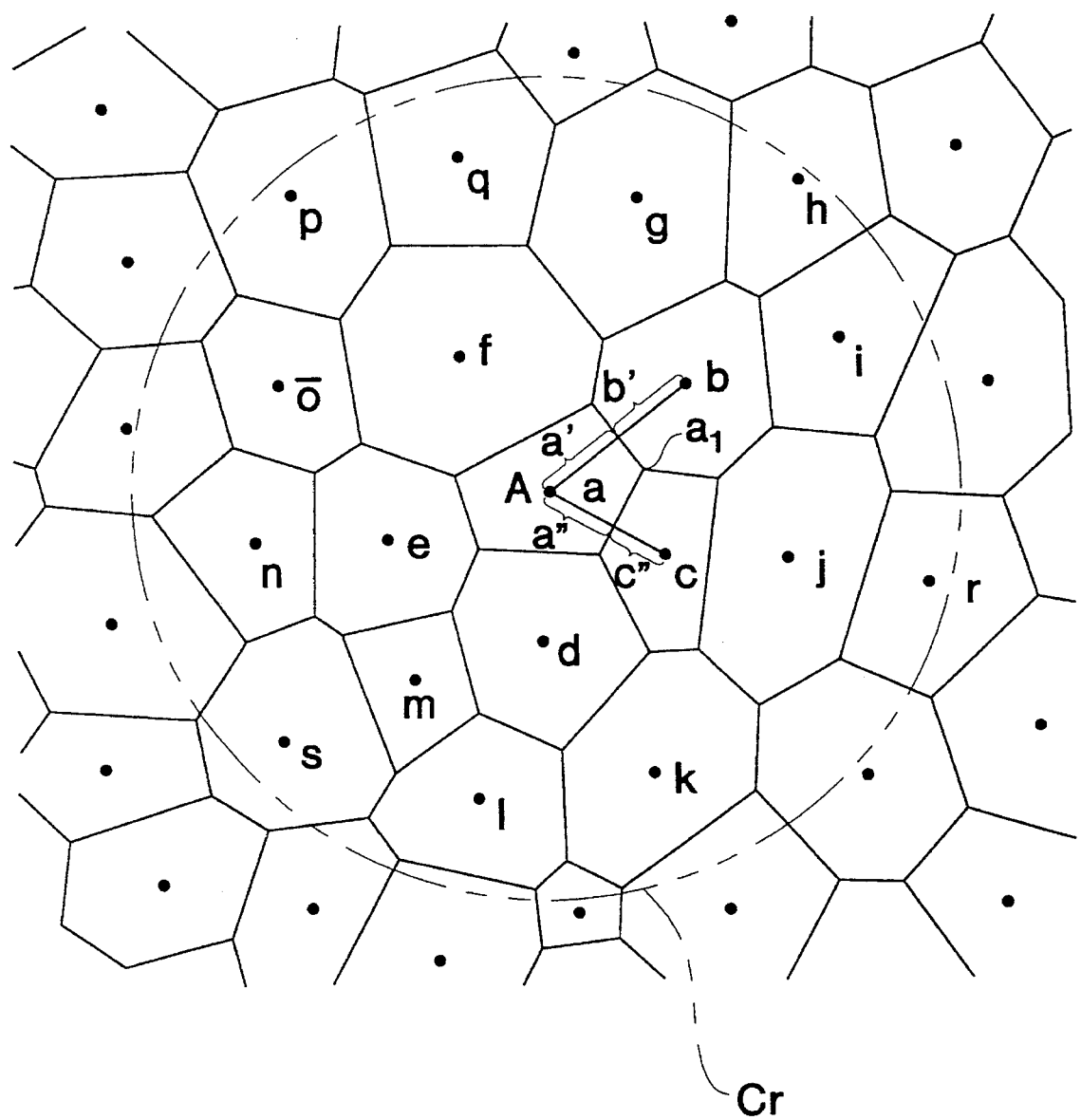
FIG. 9 illustrates determining the profile of cells by entering the center points of the cells, where A is a cornea endothelium cell; a is a center point of cell A; $a_1$ is an intersection point of a perpendicular line that proportionally divides a distance ab by average distances of ab to their peripheral points and another perpendicular line that proportionally divides a distance ac by average distances of ac to their peripheral points; b, c, d, e, f, g, h, i, j, k, l, m, n, o, p, q, r, s, are center points of additional cells; and $c_r$ is a circle whose radius is 3 times the distance ab.

The steps for computing morphological data of cells with center points of the cells of a cornea endothelium cell image entered into the computer 414 or 508 are now described with reference to flow charts (FIGS. 6 to 8) and a cell input diagram (FIG. 9).

Initially, an arbitrary cell A is selected as the first cell (n=1) (step 101), and a distance $L_{min}$=a distance ac from point a as the center point $P_n$ for n=1 to its nearest center point c is calculated (step 102). Next, center points b, c, d, e, f, g, h, i, j, k, l, m, n, o, p. q, r, and s within a circle $C_r$ whose radius is three times $L_{min}$, i.e. 3×distance ac, from the center point a are selected and reserved as quasi-peripheral points $S_m$ (step 103). Then the obtained quasi-peripheral points are sorted clockwise (according to angle), so that these peripheral points are tested in the order of g, h , b, i, r, j, c, k, d, l, m, s, e, n, o, p, f, and q (step 104), as illustrated in FIG. 9.

Next, a peripheral point of m=1, which is the first point of successive two quasi-peripheral points obtained is selected (step 105), and it is checked whether or not an angle formed by g, which is the first quasi-peripheral point $S_m$ (m=1), h, which is the second quasi-peripheral point $S_{m+1}$ (m=1), and a, which is the center point $P_n$, i.e. ∠gah, is greater than 100 degrees (step 106). If it is greater than 100 degrees, the point $P_n$ is stored as a center point of a second type peripheral cell (step 107). However, since the angle ∠gah is not greater than 100 degrees, it is further checked whether or not the angle is less than 30 degrees (step 108). If it is not less than 30 degrees, g and h will remain as quasi-peripheral points and m is incremented by one (step 113). Then it is determined whether or not the test for all the quasi-peripheral points has been completed (step 112). Since the angle ∠gah is less than 30 degrees, a comparison is made between two distances, i.e. a distance ag ($P_nS_m$) and ah ($P_nS_{m+1}$), both of which are distances from the center point a (step 109). If the distance $P_nS_m$ is greater than the distance $P_nS_{m+1}$, $S_m$ (m=1) is excluded from the quasi-peripheral points, in which case all the quasi-peripheral points that follow $S_{m+1}$ are moved up, for example $S_{m+1}$ to $S_m$, $S_{m+2}$ to $S_{m+1}$, $S_{m+3}$ to $S_{m+2}$, . . . , so as to compensate for the excluded $S_m$ (step 110). Then it is checked whether or not all the quasi-peripheral points have been completed (step 112), and thereafter the processing moves to a test for h ($S_m$) which is the new first quasi-peripheral point. Since the distance ah is longer than the distance ag, the point h ($S_{m+1}$) is excluded and g ($S_m$) is left as a quasi-peripheral point and all the quasi-peripheral points that follow $S_{m+1}$ are moved up by one, for example, $S_{m+2}$ to $S_{m+1}$, $S_{m+3}$ to $S_{m+2}$, $S_{m+4}$ to $S_{m+3}$, . . . , to compensate for the excluded $S_{m+1}$ (step 111). Then it is checked whether or not the test for all the quasi-peripheral points has been completed (step 112). Next, since the angle formed by g, which is the first quasi-peripheral point $S_m$ (m=1), b, which is the new second quasi-peripheral point $S_{m+1}$ (m=1), and a, which is the center point $P_n$ i.e., ∠gab is greater than 30 degrees (step 108), b is left as a quasi-peripheral point and m is increased by 1 (step 113). Then it is checked whether or not the test for all the quasi-peripheral points has been completed (step 112). Thereafter the processing moves to a test for b, which is the new first quasi-peripheral point $S_m$ (m=2). Since the angle formed by b, which is the first quasi-peripheral point $S_m$ (m=2), i, which is the second quasi-peripheral point $S_{m+1}$ (m=2), and a, which is the center point $P_n$, i.e. ∠bai is less than 30 degrees (step 108) and further the distance ai is longer than the distance ab (step 109), i is excluded and b is left as a quasi-peripheral point and all the quasi-peripheral points that follow $S_{m+2}$ are moved up, for example, $S_{m+2}$ to $S_{m+1}$, $S_{m+3}$ to $S_{m+2}$, $S_{m+4}$ to $S_{m+3}$, . . . , so as to compensate for the excluded $S_{m+1}$ (step 111).

Then it is checked whether or not the test for all the quasi-peripheral points has been completed (step 112). Thereafter the processing moves to a test for b, which is the first quasi-peripheral point $S_m$ (m=2). Next, since the angle formed by b, which is the first quasi-peripheral point $S_m$ (m=2), r, which is the second quasi-peripheral point $S_{m+1}$ (m=2), and a, which is the center point $P_n$ i.e. the angle ∠bar is greater than 30 (step 108), r is left as a quasi-peripheral point. Also, since the angle ∠raj is less than 30 degrees (step 108) and the distance ar is longer than distance aj (step 109), r is excluded and j is left as a quasi-peripheral point. In this manner each of the sorted quasi-peripheral points are checked, and the above steps are repeated until all the quasi-peripheral points are checked (step 112). As a result, the points, g, b, c, d, m, e, o, and f are stored as the remaining quasi-peripheral points.

Of the remaining quasi-peripheral points, with respect to successive three quasi-peripheral points, a quasi-peripheral point of m=1, which is the first point, is selected (step 114 in FIG. 7), and a comparison is made to check whether or not an angle ∠$S_m P_n S_{m+2}$ formed by the first quasi-peripheral points $S_m$, the third quasi-peripheral point $S_{m+2}$, and the center point $P_n$ is greater than 128 degrees (step 115). In this comparison, if the angle is greater than 128 degrees, the second quasi-peripheral points $S_{m+1}$ is not excluded from the stored peripheral points and the value of m is increased by 1 (step 119). Conversely, if the angle is not greater than 128 degrees, a comparison is made to check whether or not a distance $S_m S_{m+2}$ between the first quasi-peripheral points $S_m$ and the third quasi-peripheral points $S_{m+2}$ is shorter than a distance $P_n S_{m+1}$ between the center point $P_n$ and the second quasi-peripheral point $S_{m+1}$ (step 116). If the distance $S_m S_{m+2}$ is shorter than the distance $P_n S_{m+1}$, the second quasi-peripheral point $S_{m+1}$ is excluded from the stored peripheral points and all the remaining quasi-peripheral points following $S_{m+1}$ are shifted by 1 for example, $S_{m+2}$ to $S_{m+1}$, $S_{m+3}$ to $S_{m+2}$, $S_{m+4}$ to $S_{m+3}$, . . . , in order to compensate for the excluded $S_{m+1}$ (step 117).

In the case of the successive three quasi-peripheral points g ($S_m$), b ($S_{m+1}$), and c ($S_{m+2}$), since ∠gac<128° (step 115) the distance gc and the distance ab are compared with each other (step 116), where the distance ab<the distance gc, so that b is left as an actual peripheral point and the value of m is raised by 1 (step 19). Next, since the angle ∠bad is greater than 128 degrees, c is left as an actual peripheral point and the value of m is increased by 1. The next angle ∠cam is less than 128 degrees but the distance ad is shorter than the distance cm, and therefore d is left as an actual peripheral point. The angle ∠dae is less than 128 degrees, however, the distance am is longer than the distance de, and in this case, m is excluded from the actual peripheral points. In this way, the above described steps are repeated until all actual peripheral points are obtained (step 118). As a result, where $P_n$ is the center point a, of cell A, actual peripheral points b, c, d, e, and f are obtained and these peripheral points are stored (step 120). In the same manner, the peripheral points, which include the peripheral points of the second-type peripheral cells obtained by step 107, are stored for each center point of all the cells continuously extending in a two dimensional pattern (step 121).

After step 121 is completed, the average distances between the center points and the actual peripheral points are calculated and stored for all the center points of the cells, except for the second-type peripheral cells (step 123). The average distance between the center point and the actual peripheral points for Cell A, for example, is the sum of the distances from the center point, a, to the peripheral points b, c, d, e and f divided by the number of the peripheral points. Then, starting with a cell (n=1) (step 124), it is checked whether or not the center point $p_n$ is a second-type peripheral point of a peripheral cell (step 125). When $P_n$ is not a second-type peripheral point, starting with the first peripheral point $S_m$ (m=1) (step 126) of $P_n$, a point of intersection of the first perpendicular line, which perpendicularly intersects the line $P_n S_m$ at the first dividing point divided with the ratio of the average distance about the point $P_n$ obtained by step 123 and the average distance about the point $S_m$ and the second perpendicular line, which perpendicularly intersects the line $P_n S_{m+1}$ at the second dividing point divided with the ratio of the average distance about $P_n$ and the average distance about $S_{m+1}$ is calculated, and then the intersecting point of the first perpendicular line and the second perpendicular line is stored as a vertex of the cell whose center point is $P_n$ (step 127). In this case, if $P_n$ is the center point, a, of the cell A, the intersection point $a_1$ of the first perpendicular line to the line ab, passing through the first dividing point on the line ab, such that the line ab is divided in proportion with the average distance from the center point a to its peripheral points and the average distance from the center point b to its peripheral points, i.e. dividing at a ratio of a', b', and the second perpendicular line to the line ac, passing through the second dividing point on the line ac, such that the line ac is divided in proportion with the average distance from the center point a to its peripheral points and the average distance from the center point c to its peripheral points, i.e. dividing at a ratio of a": c", is calculated and stored as one vertex of the cell A. In more detail, a': b'=average distance from the center point a to this peripheral points:average distance from the center point b to its peripheral points, and a": c"=average distance from a to its peripheral points:average distance from c to its peripheral points. It has been found experimentally that the proportional division, if valued with the second to the fourth power of the average distances is applied (e.g. if the ratio of the average distances is 5:6, then the ratio of squaring is 25:36), can be well fitted to actual cases. The steps for determining all the vertices of Cell A are executed about all the peripheral points of the center point a (step 128 and step 129) and a pentagonal cell profile of Cell A, whose center point is a, is obtained.

The steps for determining the form of a cell by determining the vertices of the profile of the cell are effected for all the center points of the two-dimensionally continuous cells (step 130 and step 131). Thus, from the vertices obtained for all the center points with peripheral points excluded, the whole morphological dat such as average cell area, cell density, and hexagonal cell frequency are calculated by the above-mentioned equations of Equations 1 through 6.

In the above embodiments, morphological data on cornea endothelium cells have been computed by making analysis on a specular microscopy, which is a cornea endothelium cell photograph, with a video camera or a digitizer. However, it is also possible that, with a video camera loaded directly on a specular microscope, which is an eyeball microscope, an image signal from the camera is stored in a frame memory and analyzed to compute the aforementioned morphological data. The arrangement may be modified in various ways without departing the scope of the spirit of the present invention.

According to the method for computing morphology of cornea endothelium cells of the present invention, in quantitatively computer morphology of cornea endothelium cells in the process of cornea endothelium cell checkup which is effected before and after a cataract operation, all the disadvantages that the conventional computation methods have had can be solved, and all morphological data necessary for clinical treatment can be easily obtained with far less labor than in the digitizer method that allows particularly accurate decision data to be obtained.

According to the present invention, peripheral points, which are cell centers on the periphery of center points of the cells entered into the computer, can be determined efficiently without omissions. Thus, the time for computation can be reduced in computing the morphology of the cells.

According to the present invention, exclusion of unnecessary peripheral points from a large number of peripheral points including actual peripheral points on the periphery of a center point of one cell can be accomplished in a fashion well matched to actual cases.

According to the present invention, in excluding unnecessary peripheral points from a large number of peripheral points on the periphery of the center point of the one cell, if the center point of the one cell is the center point of a peripheral cell, the unnecessary peripheral points can be selected in a fashion well matched to actual cases. Therefore, the work of exclusion for the center point may be saved, so that the exclusion of unnecessary peripheral points can be accomplished efficiently.

According to the present invention, in determining actual peripheral points by excluding unnecessary peripheral points from successive three peripheral points on the periphery of a center point of one cell, actual peripheral points can be determined easily and efficiently in a fashion well matched to actual cases.

According to the present invention, in determining a perpendicular line that proportionally divides a distance between a center point of one cell and a peripheral point thereof by their average distances to the peripheral points, for each of successive peripheral points, and then determining an intersection point of the perpendicular lines as a vertex of the profile of the cell, vertices that are well matched to actual cases can be determined.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method of quantitatively determining morphology of a plurality of cells, comprising:
    (a) representing center points of the plurality of cells in a two-dimensional coordinate array;
    (b) determining peripheral points, said peripheral points being center points of the plurality of cells falling within a specified distance from a center point of a selected one of the plurality of cells;
    (c) sorting the peripheral points into a first arrangement in a predetermined direction with respect to the center point of the selected one of the plurality of cells;
    (d) excluding a further of two successive peripheral points one after another, from the first arrangement to form a second arrangement, if an angle formed by the two successive peripheral points and the center point is less than a specified angle;
    (e) excluding a second of three successive peripheral points one after another, from the second arrangement if a distance between the first successive peripheral point and the third successive peripheral point is less than a distance between the center point and the second successive peripheral point;
    (f) storing peripheral points which were not excluded from the second arrangement in said step (e), as remaining peripheral points of the center point of the selected one of the plurality of cells;
    (g) determining an average distance from the center point of the selected one of the plurality of cells to the remaining peripheral points;
    (h) determining average distances from between the center point of the selected one of the plurality of cells for each remaining cell of the plurality of cells to the remaining peripheral points by repeating steps (b)–(g);
    (i) defining perpendicular lines which perpendicularly and proportionally divide lines defined by a center point of a new selected one of the plurality of cells and the remaining peripheral points thereof by the average distances obtained in said step (h);
    (j) defining vertices of the new selected one of the plurality of cells where the perpendicular lines intersect;
    (k) defining vertices of each remaining cell of the plurality of cells by repeating steps (i)–(j); and
    (l) determining the morphology of the plurality of cells from coordinates of the vertices of each of the plurality of cells.

2. The method of claim 1, wherein the specified distance is of 2.5 to 3.5 times a distance from the center point to a closest peripheral point.

3. The method of claim 1, wherein the specified angle is 20 to 40 degrees.

4. The method of claim 1, wherein between said steps (c) and (d) if the angle formed by the two successive peripheral points and the center point is greater than 90 to 110 degrees, the center point is stored as a center point of an outer peripheral cell.

5. The method of claim 1, wherein said steps (d) and (e), when an angle formed by the first successive peripheral point, the center point, and the third successive peripheral point is greater than 120 to 140 degrees, the second peripheral point is retained.

6. The method of claim 1, wherein the perpendicular lines in said step (i) are defined by proportionally dividing the distances between the center point and the remaining peripheral points.

7. The method of claim 1, wherein the plurality of cells are cornea endothelium cells.

8. The method of claim 1, wherein the morphology of the plurality of cells comprises at least one characteristic selected from a group of characteristics that includes cell area, an average cell area, a cell density, a standard deviation, a coefficient of variation and a hexagonal cell frequency.

9. A method of quantitatively determining morphology of a plurality of cells, comprising:

(a) determining peripheral points within a specified distance from a center point of a selected one of the plurality of cells;

(b) sorting the peripheral points in a predetermined direction;

(c) determining an angle formed by first and second successive peripheral points in the predetermined direction and the center point;

(d) excluding one of the first and second successive peripheral points which is further from the center point, if the angle is less than a specified angle;

(e) determining a first distance between the first successive peripheral point and a third successive peripheral point in the predetermined direction and a second distance between the center point and the second successive peripheral point;

(f) excluding the second successive peripheral point if the first distance is less than the second distance;

(g) repeating steps (a)–(f) for remaining cells surrounding the selected one of the plurality of cells;

(h) determining an average distance between remaining peripheral points and the center point of the selected one of the plurality of cells and determining average distances between remaining peripheral points and center points of remaining cells surrounding the selected one of the plurality of cells;

(i) determining a first divisional point on a first line, wherein said first line connects the center point of the selected one of the plurality of cells and a first remaining peripheral point of a first remaining peripheral cell; and said first divisional point proportionally divides said first line according to a proportion of the average distance of the selected one of the plurality of cells and an average distance of the first remaining peripheral cell and determining a first perpendicular line, which perpendicularly intersects the first line at the first divisional point;

(j) determining a second divisional point on a second line, wherein said second line connects the center point of the selected one of the plurality of cells and a second remaining peripheral point of a second remaining peripheral cell; and said second divisional point proportionally divides said second line according to a portion of the average distance of the selected one of the plurality of cells and an average distance of the second remaining peripheral cell and determining a second perpendicular line, which perpendicularly intersects said second line at the second divisional point;

(k) determining a first vertex of the selected one of the plurality of cells said first vertex being an intersection of the first perpendicular line and the second perpendicular line;

(l) repeating steps (i)–(k) for each remaining peripheral point to determine all vertices of the selected one of the plurality of cells;

(m) repeating steps (a)–(l) for each remaining cell of the plurality of cells; and (n) determining the morphology of the plurality of cells from coordinates of all vertices of each of the plurality of cells.

10. The method of claim 9, wherein the specified distance is of 2.5 to 3.5 times a distance from the center point to a closest peripheral point.

11. The method of claim 9, wherein the specified angle is 20 to 40 degrees.

12. The method of claim 9, wherein if the angle formed by the first and second peripheral points in the predetermined direction and the center point is greater than 90 to 110 degrees, the center point is a center point of a peripheral cell.

13. The method of claim 9, wherein when an angle formed by the first successive peripheral point, the center point, and the third successive peripheral point is greater than 120 to 140 degrees, the second peripheral point is retained.

14. The method of claim 9, wherein the first and second points in said steps (i) and (j) are determined by proportionally dividing the distances between the center point and the remaining peripheral points.

15. The method of claim 9, wherein the plurality of cells are cornea endothelium cells.

16. The method of claim 9, wherein the morphology of the plurality of cells comprises at least one characteristic selected from a group of characteristics that include cell area, an average cell area, a cell density, a standard deviation, a coefficient of variation and a hexagonal cell frequency.

* * * * *